United States Patent
Hasegawa et al.

(10) Patent No.: US 7,056,425 B2
(45) Date of Patent: Jun. 6, 2006

(54) BIOSENSOR

(75) Inventors: Miwa Hasegawa, Hyogo (JP); Tomohiro Yamamoto, Hirakata (JP); Shin Ikeda, Katano (JP); Toshihiko Yoshioka, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 295 days.

(21) Appl. No.: 10/469,522

(22) PCT Filed: Nov. 12, 2002

(86) PCT No.: PCT/JP02/11808

§ 371 (c)(1),
(2), (4) Date: Sep. 2, 2003

(87) PCT Pub. No.: WO03/042679

PCT Pub. Date: May 22, 2003

(65) Prior Publication Data

US 2004/0082045 A1    Apr. 29, 2004

(51) Int. Cl.
*G01N 27/327* (2006.01)

(52) U.S. Cl. .............. 204/403.04; 204/403.14
(58) Field of Classification Search ............... 204/403.01–403.14
See application file for complete search history.

(56) References Cited

U.S. PATENT DOCUMENTS

| 5,437,999 | A | 8/1995 | Diebold et al. |
| 5,658,444 | A | 8/1997 | Black et al. |
| 6,726,818 | B1 * | 4/2004 | Cui et al. ............ 204/403.01 |

FOREIGN PATENT DOCUMENTS

| EP | 1 118 675 A2 | 7/2001 |
| EP | 1 223 425 A1 | 7/2002 |
| EP | 1 347 292 A1 | 9/2003 |
| JP | 02-62952 | 3/1990 |
| JP | 11-304748 | 11/1999 |
| JP | 2000-116628 A * | 4/2000 |
| JP | P2000-258382 A | 9/2000 |
| JP | P2001-201480 A | 7/2001 |
| JP | P2002-202283 A | 7/2002 |
| JP | P2002-340839 A | 11/2002 |
| WO | WO 00/60340 | 10/2000 |

OTHER PUBLICATIONS

JPO computer translation of JP 2000-116628 A (Norimasa et al.).*
Shanghai Patent and Trademark Law Office; Application No. 02804432.0; Chinese Office Action; Nov. 2002.

* cited by examiner

*Primary Examiner*—Alex Noguerola
(74) *Attorney, Agent, or Firm*—McDermott Will & Emery LLP

(57) ABSTRACT

To provide an improved biosensor which allows easy addition of whole blood to the sensor and rapid supply of the added whole blood to a filter even in the case of collecting blood by fingertip centesis for measurement, a second air aperture is provided in a sample solution supply pathway including an electrode system and a reaction layer and communicating with a first air aperture on the terminal end side.

3 Claims, 5 Drawing Sheets

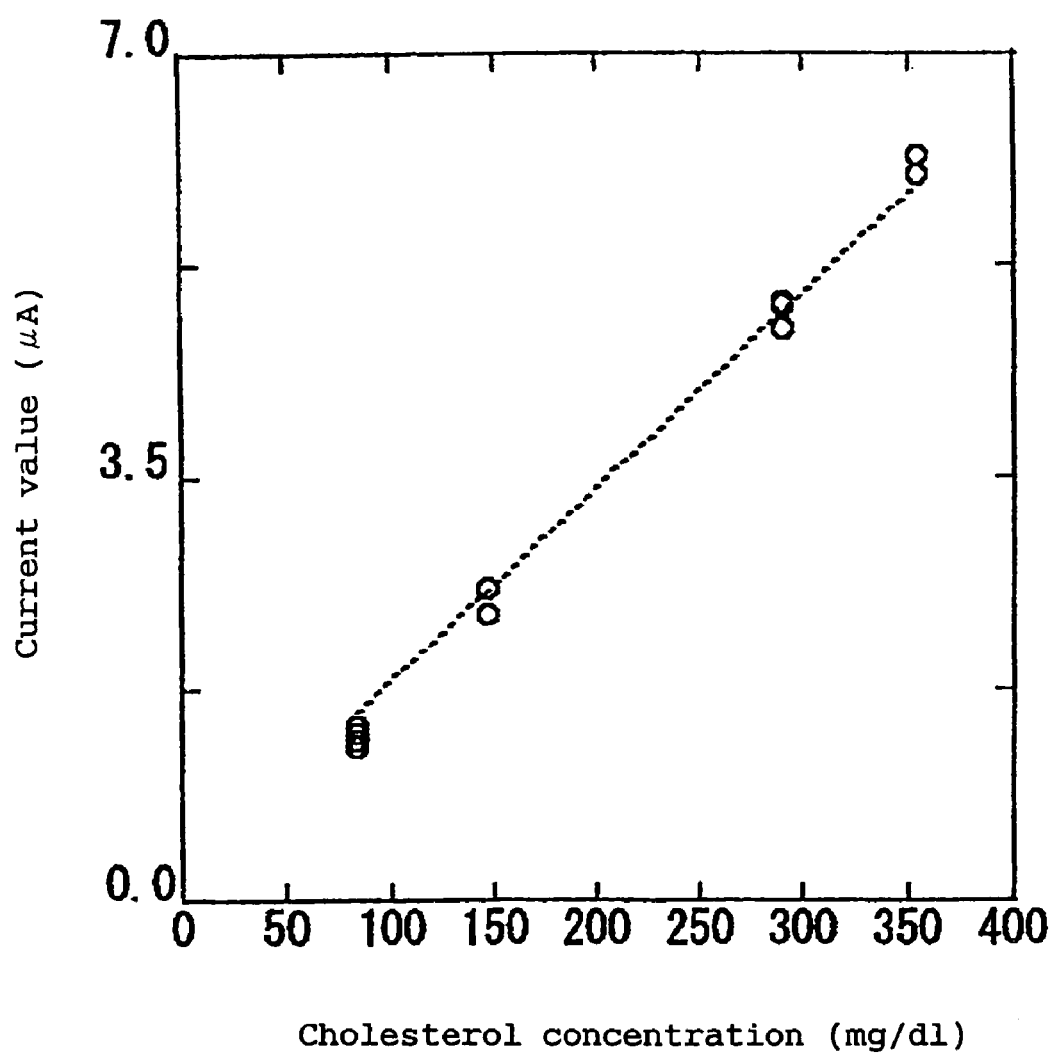
F I G. 5

BIOSENSOR

TECHNICAL FIELD

The present invention relates to a biosensor, specifically a cholesterol sensor, capable of determining the quantity of a specific component in a sample in a speedy, highly-sensitive and simple manner.

BACKGROUND ART

A description is given to an example of a conventional biosensor in terms of a glucose sensor.

A typical glucose sensor is obtained by forming an electrode system including at least a measuring electrode and a counter electrode on an insulating base plate by screen printing or the like and forming an enzyme reaction layer containing a hydrophilic polymer, oxidoreductase and an electron mediator on the electrode system. For example, glucose oxidase is used as oxidoreductase and a metal complex or an organic compound such as potassium ferricyanide, ferrocene derivatives and quinone derivatives is used as the electron mediator. A buffer is added to the enzyme reaction layer if required.

Upon dropping a sample solution containing a substrate onto the enzyme reaction layer of the biosensor, the enzyme reaction layer dissolves to cause a reaction between the enzyme and the substrate. Reduction of the electron mediator accompanies the reaction. After the enzyme reaction is completed, the reduced electron mediator is electrochemically oxidized to obtain an oxidation current value, from which the substrate concentration in the sample solution is determined.

The biosensor of this kind is theoretically capable of measuring various substances by using an enzyme of which the substrate is a measuring object. For example, if cholesterol oxidase or cholesterol dehydrogenase is used as oxidoreductase, a cholesterol value in serum, which is used as a diagnostic index in various medical institutions, can be measured.

In this case, the enzyme reaction of cholesterol esterase proceeds very slowly. Accordingly, an appropriate surfactant may be added to improve the activity of cholesterol esterase and reduce the time required for the whole reaction. However, the surfactant included in the reaction system affects adversely on hemocytes, which makes impossible to measure whole blood as done in the glucose sensor.

In response to this, a proposal has been made to provide a filter (hemocyte filtering part) in the vicinity of an opening of a sample solution supply pathway so that plasma obtained by filtering hemocytes out of the whole blood is exclusively and rapidly supplied into a sensor (sample solution supply pathway).

However, if the filter is inappropriately built in the sensor, hemocytes captured in the filter are destroyed to dissolve hemoglobin out. Thereby, filtration of the hemocyte components with the filter becomes difficult and small hemoglobin flows into the sample solution supply pathway to cause a measurement error.

This is presumably caused by the fact that a difference in thickness between the filter before absorbing a sample solution and the filter expanded after absorbing the sample solution is not fitted with a gap between pressing parts for holding the filter from the top and the bottom. When the gap between the pressing parts for holding the filter from the top and the bottom is too narrow for the thickness of the expanded filter, the expansion of the filter is prevented. The pore size of the filter thus prevented from expansion cannot be widened sufficiently, thereby the hemocytes as infiltrating thereinto are destroyed.

As opposed to this, if the gap between the upper and lower pressing parts is previously set wide for the supposed thickness of the expanded filter taking into account that the degree of the filter expansion varies depending on a hematocrit value (volume percent of red cell) different in each sample solution, it is feared that the filter may be misaligned during storage of the sensor.

It is also considered that the filter itself is made thinner than a conventional one to prevent the filter from expansion due to the absorption of the sample solution. In this case, however, if the sample solution is sucked only from an end of the filter on a primary side, the amount of the sample solution absorbed within a certain period of time is reduced as described in the specification of Japanese Patent Application No. 2000-399056. Then, the rate at which the plasma flows out of a secondary-side of the filter is reduced and the rate at which the plasma saturates the inside of the sensor, in particular the inside of the sample solution supply pathway, becomes low, which results in long measurement time.

As opposed to this, where a suction area is made wider to increase the amount of the sample solution that can be absorbed within a certain period of time and the sample solution is dropped on an upper part of the filter, the sample solution flows along the surface of the filter at a higher rate than the rate of infiltration into the filter. The sample solution having flown along the filter surface then flows into the sample solution supply pathway from an opening thereof connecting the sample solution supply pathway and the filter, which may cause a measurement error.

In the specification of Japanese Patent Application No. 2001-152868, for example, there is disclosed a technique of providing a first pressing part for holding a primary side portion of the filter from the bottom, second pressing parts for holding a secondary side portion of the filter from the top and the bottom, a third pressing part for holding a center portion of the filter from the top and a void provided between the second and third pressing parts for surrounding the filter. With this technique, the destruction of hemocytes caused by the prevention of the filter expansion is inhibited even if the gap between the pressing parts for holding the filter from the top and the bottom is not fitted with the thickness of the expanded filter. It is also described that the measurement error caused by hemocytes flown into the sample solution supply pathway along the filter surface is avoided by dropping the sample solution directly onto the filter.

In the case of a sensor to which the filter is applied, however, the plasma may spill from an air aperture in some cases depending on the viscosity of the plasma or the plasma amount in whole blood after the filtered plasma flows into and saturates the sample solution supply pathway, though the plasma is expected to stop at the air aperture. The whole blood, which is the sample solution, comprises hemocyte components and a liquid component (plasma), in which the percentage of the hemocyte components (volume percent of red cell) is in the range of about 20 to 60% though it varies among individuals. Further, the viscosity varies depending on the cholesterol concentration in the whole blood. These differences cause a problem in that the plasma travels along the electrode plate to spill from the sample solution supply pathway after reaching the air aperture if the sample solution, even of the same origin, has different flow rate or reduced viscosity and volume percent in red cell.

Hence, the present invention is intended to provide a biosensor that is improved to eliminate the above-described disadvantages and stop the plasma at the air aperture irrespective of the viscosity of the plasma in the sample solution and the plasma amount in the whole blood. Further, the present invention is intended to provide a cholesterol sensor for measuring whole blood with high accuracy and excellent response.

DISCLOSURE OF INVENTION

The present invention relates to a biosensor comprising an insulating base plate, an electrode system including a measuring electrode and a counter electrode provided on the base plate, a cover for covering the insulating base plate, at least one reaction layer containing oxidoreductase and/or an electron mediator, a sample solution supply pathway which is formed by the insulating base plate and the cover and includes the electrode system and the reaction layer, a first air aperture provided in the cover in the sample solution supply pathway, a sample solution supply part and a filter provided between the sample solution supply pathway and the sample solution supply part to filter hemocytes, the biosensor being capable of sucking plasma with hemocytes therein filtered with the filter into the sample solution supply pathway due to capillarity, characterized in that a second air aperture is provided in the insulating base plate in the sample solution supply pathway.

In the above biosensor, it is preferred that the first air aperture and the second air aperture are communicated.

BRIEF DESCRIPTION OF DRAWINGS

FIG. 3 is a schematic vertical section of the sensor excluding a reaction layer and the like.

FIG. 5 is a graph illustrating a response characteristic of a cholesterol sensor according to an example of the present invention.

BEST MODE FOR CARRYING OUT THE INVENTION

Figure 1:
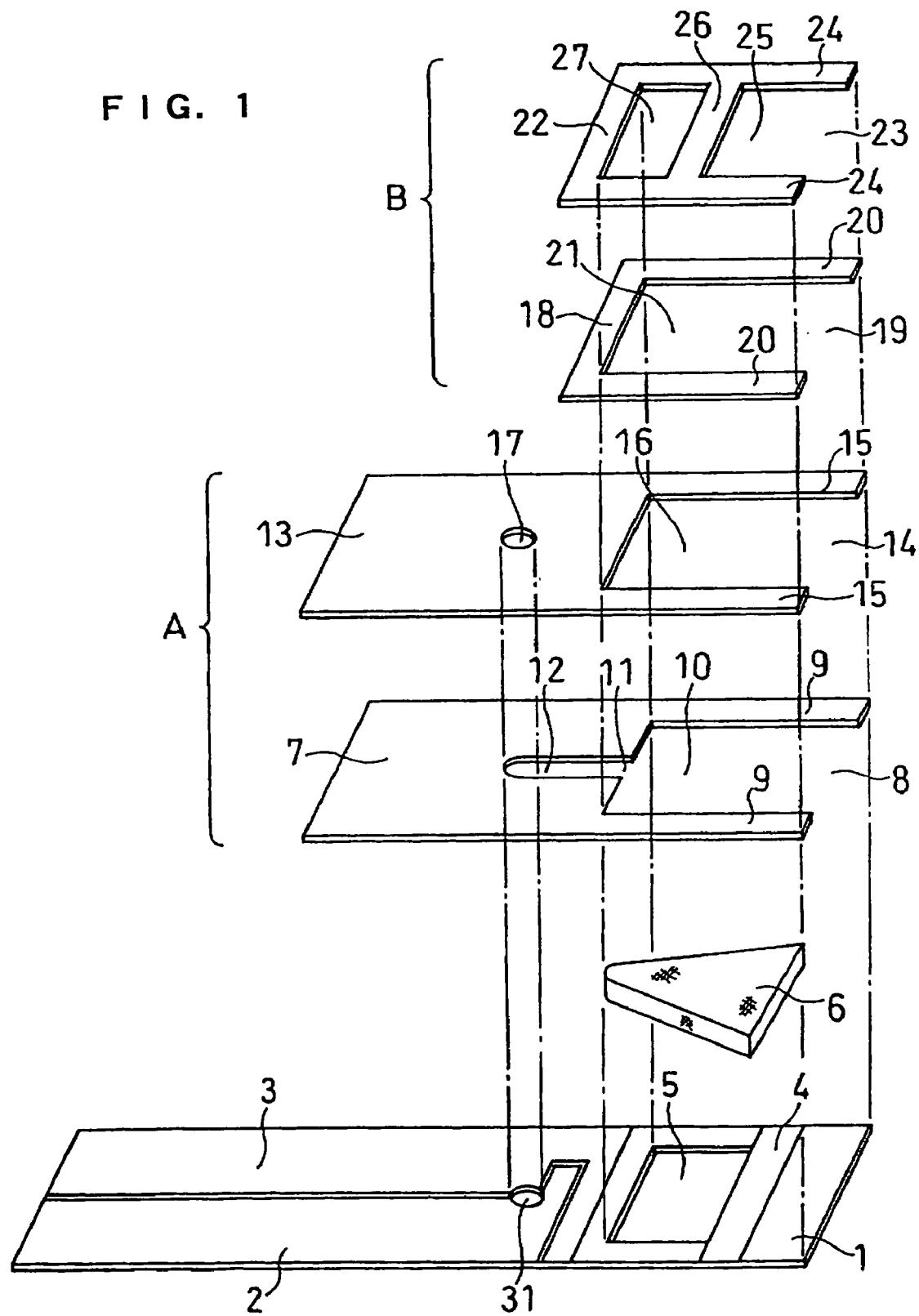
FIG. 1 is a perspective view of a disassembled biosensor according to an embodiment of the present invention.

As described above, the biosensor according to the present invention includes an electrode system and a reaction layer and has a filter for filtering hemocytes provided between a sample solution supply pathway having a first air aperture on a terminal end side and a sample solution supply part. Plasma from which hemocytes are removed by the filter is sucked into the sample solution supply pathway due to capillarity. The biosensor is characterized in that the sample solution supply pathway includes a second air aperture in addition to the first air aperture.

Further, the first air aperture is preferably communicated with the second air aperture.

With the above-described structure, the plasma can be kept in the sample solution supply pathway regardless of differences in viscosity of the plasma in the sample solution, plasma amount in whole blood and volume percent of red cell. Conventionally, the plasma flown in the pathway travels along the insulating base plate to spill from the sample solution supply pathway together with a reagent upon reaching the air aperture, thereby causing a measurement error. However, with the second air aperture opened in the insulating base plate to communicate with the first air aperture, the sample solution is prevented from traveling along the insulating base plate and spilling from the sample solution supply pathway. Thereby, the volume of a filtrate to be measured is automatically determined irrespective of the viscosity of the sample solution and the percentage of sample components to be filtered. This makes possible to resolve the measurement error. Further, since the sample solution exists only in the sample solution supply pathway, the possibility of contamination of the other parts than the sensor (measurement devices and a measurer) is reduced.

The electron mediator used in the present invention may be selected from, besides potassium ferricyanide, redox compounds having electron transferring ability to and from oxidoreductase such as cholesterol oxidase.

Oxidoreductase is an enzyme of which the substrate is a measuring object. In a sensor whose measuring object is glucose, glucose oxidase is used. In order to measure a cholesterol value in serum, which is used as a diagnostic index, are used cholesterol oxidase or cholesterol dehydrogenase which is an enzyme for catalyzing oxidative reaction of cholesterol and cholesterol esterase which is an enzyme for catalyzing a process of converting cholesterol ester into cholesterol. Since the enzyme reaction of cholesterol esterase proceeds very slowly, an appropriate surfactant may be added, for example, to improve the activity of cholesterol esterase and reduce the time required for the whole reaction.

A layer containing the electron mediator and a reaction layer containing oxidoreductase are arranged on or in the vicinity of the electrode system in the sensor. In a sensor including a covering member, which is combined with the base plate having the electrode system provided thereon to form therebetween a sample solution supply pathway for supplying a sample solution to the electrode system, the reaction layer may be arranged on a portion exposed to the sample solution supply pathway or an opening of the sample solution supply pathway. In either position, it is preferred that the reaction layer is easily dissolved by the introduced sample solution to reach the electrode system.

For the purpose of protecting the electrodes and inhibiting the reaction layer to be formed from peeling, a hydrophilic polymer layer is preferably formed on the electrode system. Other than on the electrode system, the hydrophilic polymer layer is preferably formed as a base for forming the reaction layer or a hydrophilic polymer may be contained in the reaction layer lying at the bottom.

Above all, it is preferable that the reaction layer containing the electron mediator is separated from the surfactant to enhance the solubility of the reaction layer. It is also preferable that the electron mediator is separated from cholesterol oxidase and cholesterol esterase, which are enzymes for catalyzing the oxidative reaction of cholesterol, in view of stability during storage.

There is an example of a biosensor for measuring blood sugar level in which a lipid-containing layer is formed to cover the layers formed on the electrode system such that the sample solution is introduced to the reaction layer (for example, Japanese Laid-Open Patent Publication No. HEI 2-0062952). In the biosensor according to the present invention for measuring cholesterol, it is preferred that part of the reaction layer is formed by a freeze drying method (e.g., the specification of Japanese Patent Application No. 2000-018834) or the surface of the covering member is given hydrophilicity by means of a surfactant or plasma irradiation. Such a structure can eliminate the need of forming the lipid layer.

As the hydrophilic polymer, for example, may be used water-soluble cellulose derivatives, in particular ethyl cellulose, hydroxypropyl cellulose, carboxymethyl cellulose, polyvinylpyrrolidone, polyvinyl alcohol, gelatin, agarose, polyacrylic acid or salts thereof, starch or derivatives thereof, polymers of maleic anhydride or salts thereof, polyacrylamide, methacrylate resin and poly-2-hydroxyethyl methacrylate.

As the surfactant, for example, may be used n-octyl-β-D-thioglucoside, polyethylene glycol monododecyl ether, sodium cholate, dodecyl-β-maltoside, sucrose monolaurate, sodium deoxycholate, sodium taurodeoxycholate, N,N-bis (3-D-gluconamidopropyl)deoxycholamide and polyoxyethylene (10) octyl phenyl ether.

In the case of using lipid, amphipathic phospholipid such as lecithin, phosphatidyl choline and phosphatidylethanolamine is favorably used.

An oxidation current may be measured by a measurement method on a two-electrode system using only a measuring electrode and a counter electrode or a three-electrode system using a reference electrode in addition, among which the three-electrode system allows measurement with greater accuracy.

Hereinafter, the present invention will be detailed by way of specific embodiments with reference to the figures. FIG. 1 is a perspective view of a disassembled biosensor according to a preferred embodiment of the present invention.

In the biosensor shown in FIG. 1, an electrode system including a working electrode 2 and a counter electrode 3 is formed by sputtering using palladium and subsequent laser trimming on the left side of an insulating base plate 1 made of insulating resin such as polyethylene terephthalate. An area of the electrodes is determined in correspondence with a width of a slit 12 formed in a spacer 7 to be described later. The insulating base plate 1 also includes an adhesive part 4 and an aperture 5. The adhesive part 4 may be provided by applying, for example, a double-stick tape on the insulating base plate 1.

The spacer 7 is provided with an opening 10 for accommodating a filter 6 therein, a slit 12 for forming a sample solution supply pathway 12', rails 9 formed on both sides of the slit 12 to introduce a sample solution into a primary side portion of the filter and a connecting part 11 for connecting the opening 10 and the slit 12.

A cover 13 includes a first air aperture 17, an opening 16 and rails 15 formed on both sides of the opening 16 to introduce the sample solution into the primary side portion of the filter.

A spacer 18 includes an opening 21 for accommodating the filter 6 therein and rails 20 formed on both sides of the opening 21 to introduce the sample solution into the primary side portion of the filter.

A cover 22 includes an opening 25 for accommodating the filter 6 therein, a pressing part (dividing part) 26, an aperture 27 and rails 24 formed on both sides of the opening 25 to introduce the sample solution into the primary side portion of the filter.

Upon integrating the members shown in FIG. 1, the opening 10 in the spacer 7, the opening 16 in the cover 13, the opening 21 in the spacer 18 and the opening 25 in the cover 22 shown in FIG. 1 are communicated. Further, a second air aperture 31 in the insulating base plate 1, a terminal end of the slit 12 in the spacer 7 and the first air aperture 17 in the cover 13 are communicated.

The filter 6 is made of glass fiber filter paper and has an isosceles triangle shape as viewed in a projection on a plane identical to the insulating base plate 1 shown in FIG. 1.

In assembling the sensor, first, the cover 13 is placed on the spacer 7 in a positional relationship as indicated by dashed lines in FIG. 1 to obtain a joint base plate A. At this time, the slit 12 forms a concave portion in the cover 13 and the spacer 7 thus jointed, in which a reaction layer is formed as described later.

Then, the cover 22 is placed on the spacer 18 in a positional relationship as indicated by dashed lines in FIG. 1 to obtain a joint base plate B.

Further, the insulating base plate 1 and the joint base plates A and B are assembled in a positional relationship as indicated by dashed lines in FIG. 1 and the filter 6 is mounted thereon in such a manner that the filter 6 having an almost isosceles triangle shape in a projection on a plane identical to the insulating base plate 1 contacts the adhesive part 4 of the insulating base plate 1 at the right end on the primary side (bottom side).

In other words, the right end on the primary side (bottom side) of the filter 6 enters a state of being disposed on the insulating base plate 1 and fitted into the opening 10 of the spacer 7, the opening 16 of the cover 13, the opening 21 of the spacer 18 and the opening 25 of the cover 22. The left end on a secondary side (vertex side) of the filter 6 is brought into a state of being sandwiched between the connecting part 11 in the concave portion of the joint base plate A and the insulating base plate 1.

Figure 2:
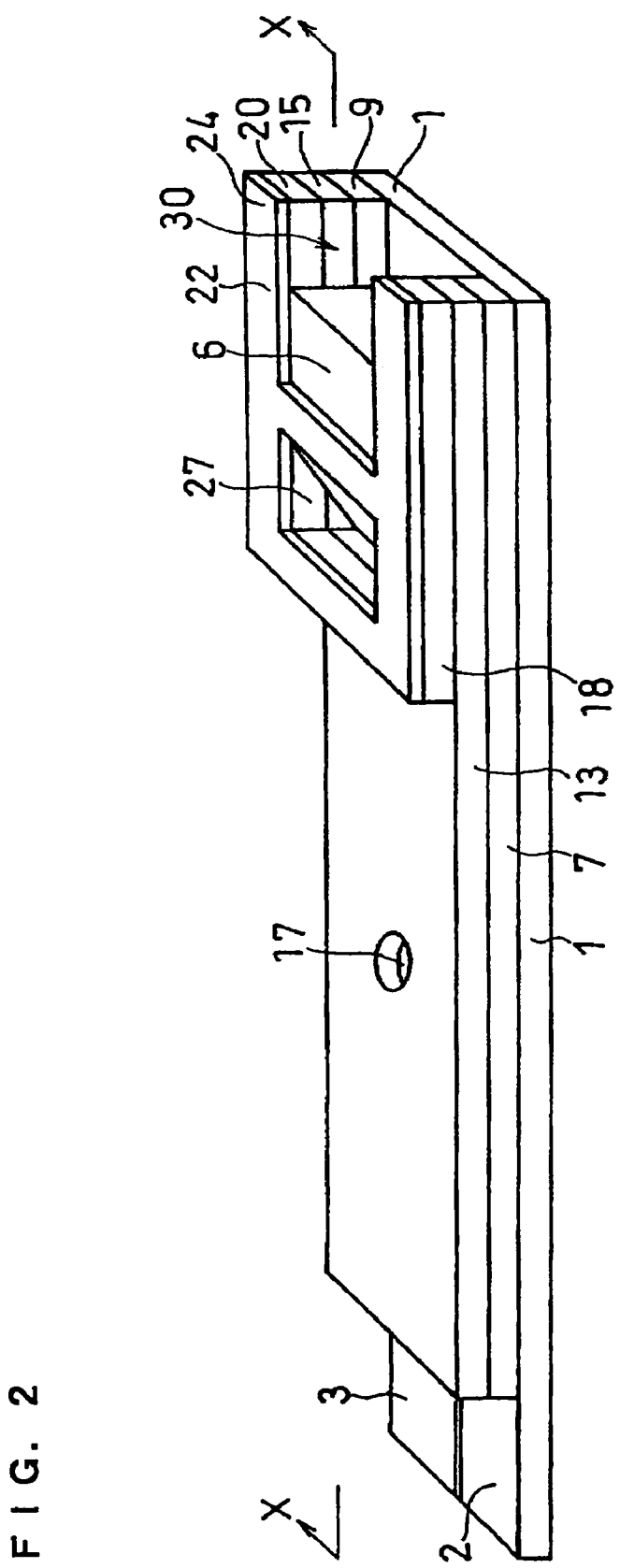
FIG. 2 is a perspective view of an assembled biosensor according to an embodiment of the present invention.
Figure 3:
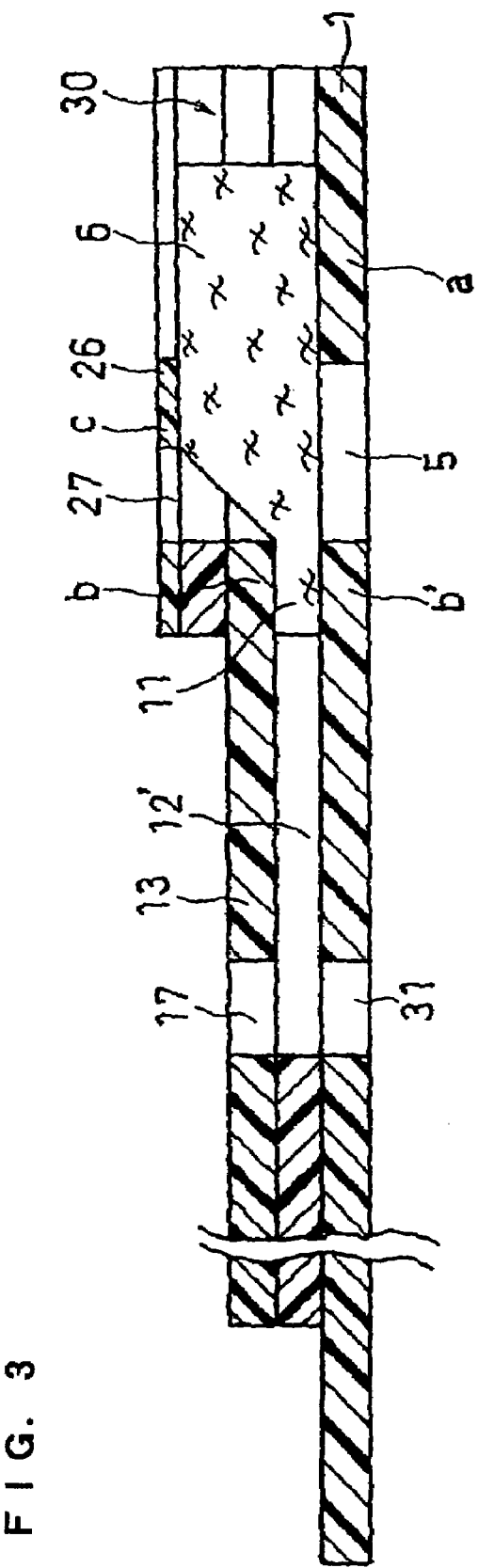

FIG. 2 shows a schematic perspective view of the thus obtained biosensor according to the present invention and FIG. 3 shows its structure in section. FIG. 3 is a schematic vertical section of the biosensor according to the present invention taken along the line X—X shown in FIG. 2. In FIG. 3, reaction layers and the like provided in the sample solution supply pathway 12' are omitted.

In the biosensor of the present invention shown in FIGS. 1 to 3, apertures 5 and 27 are formed as shown in FIG. 3, in which the filter 6 is not in contact with the other members.

That is, the biosensor of the present invention includes, as shown in FIG. 3, a first pressing part a for holding the primary side portion of the filter 6 from the bottom, second pressing parts b and b' for holding the secondary side portion of the filter 6 from the top and the bottom and a third pressing part c for holding the center of the filter 6 from the top.

Between the second pressing parts b and b' and the third pressing part c, the apertures 5 and 27 are communicated via the openings 10, 16 and 21 (see FIG. 1) to make the filter 6 not contact the other members.

Further, opening ends 8, 14, 19 and 23 shown in FIG. 1 are also communicated to form a concave portion which serves as a sample solution supply part 30 as shown in FIG. 2. In the biosensor of the present invention, the existence of the concave portion makes an end face of the sensor open (open to the outside). Therefore, as a method of adding the sample solution, for example, a fingertip stung to bleed may be rubbed against the sample solution supply part 30. The sample solution is temporarily held in the concave portion and then supplied rapidly and intensively to the primary side of the filter.

Figure 4:
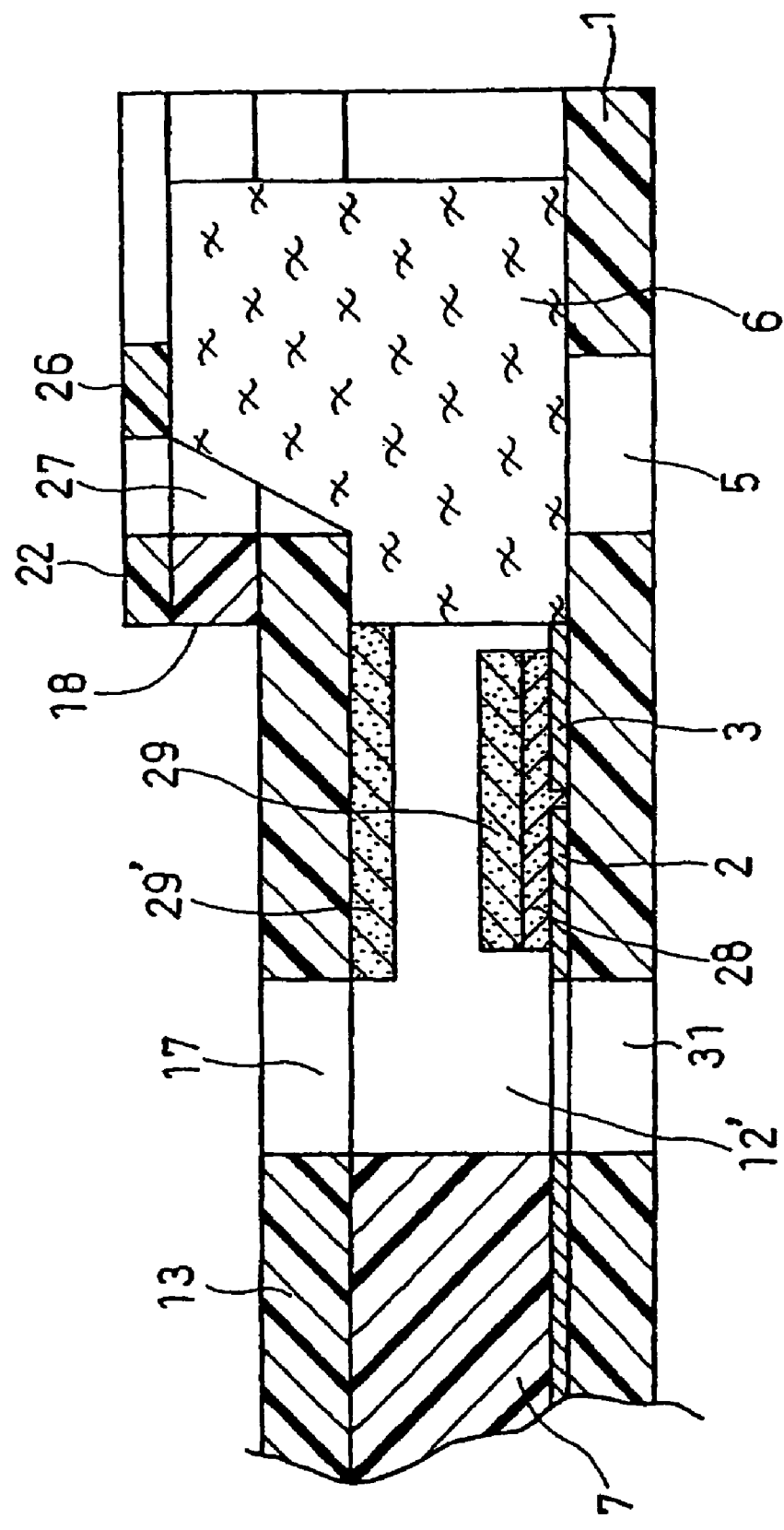
FIG. 4 is a schematic vertical section illustrating the vicinity of an electrode system of the sensor.

FIG. 4 shows a schematic vertical section illustrating another embodiment of the biosensor of the present invention. The reaction layers and the electrode system omitted in FIG. 3 are depicted in FIG. 4. On the electrode system (2 and 3) of the insulating base plate 1, a hydrophilic polymer layer 28 and a reaction layer 29 are formed. In addition, a reaction layer 29' is formed on the underside of the cover 13 corresponding to a ceiling of the sample solution supply pathway 12'. Other members shown in FIG. 4 are the same as those shown in FIG. 3.

The biosensor shown in FIGS. 1 to 4 is made of six members including the filter and various base plates for easy explanation of the structure. However, the cover 22 and the spacer 18 or the cover 13 and the spacer 7 may be formed as a single member.

In measuring cholesterol in blood with this sensor, whole blood is supplied from the sample solution supply part 30, the concave portion, to the filter 6. At this time, since the spacer 7, the cover 13, the spacer 18 and the cover 22 contact the sample solution supply part 30 at the rails 9, 15, 20 and 24, the whole blood is efficiently supplied to the filter 6.

The supplied blood permeates into the filter 6 from the end face and the top face on the primary side. In the filter 6, since the permeation rate of hemocytes is lower than that of plasma which is a liquid component, the plasma seeps from the tip of the filter 6 on the secondary side. The seeped plasma fills the vicinity of the electrode system and the entire sample solution supply pathway 12' extending to the connecting part between the first and second air apertures 17 and 31 while dissolving the reaction layer carried on a position covering the electrode system and/or the underside of the cover 13.

Once the entire sample solution supply pathway 12' is filled up, the liquid flow in the filter 6 stops. At this time, the hemocytes remain in the filter 6 without reaching the secondary side end of the filter 6. It is therefore necessary to design the filter 6 to give a difference in flow resistance between the plasma and the hemocytes to such an extent that the hemocytes do not reach the secondary side end of the filter 6 even if the plasma are passed in an amount enough to fill the sample solution supply pathway 12'.

A depth filter having a pore diameter of 1 to 7 µm is suitably used as the filter of the present invention. The thickness of the filter is preferably 300 to 400 µm.

Through the process of hemocyte filtration, a chemical reaction occurs between the reaction layer dissolved by the plasma and a component to be measured in the plasma (cholesterol in using a cholesterol sensor). After an elapse of a predetermined time, a current value is measured by electrode reaction to determine the quantity of the component in the plasma.

FIG. 4 shows an example of how the reaction layers are arranged in the vicinity of the electrode system in the sample solution supply pathway 12'. On the electrode system on the insulating base plate 1, are formed a hydrophilic polymer layer 28 containing sodium salt of carboxymethyl cellulose (hereinafter simply referred to as "CMC") and a reaction layer 29 containing a reaction reagent such as an electron mediator. In the sample solution supply pathway 12' formed by combining the cover 13 and the spacer 7, a reaction layer 29' containing oxidoreductase is formed on the surface of the cover 13 exposed to the sample solution supply pathway 12'.

As shown in FIGS. 1 to 4, in the sample solution supply pathway 12', a distance in a direction vertical to the liquid flow is made smaller than the thickness of the primary side portion of the filter 6, whereas a portion of 1 mm from the secondary side end of the filter 6 is compressed to be positioned in the vicinity of the connecting part 11 of the sample solution supply pathway 12'.

The compressed portion of the filter 6 preferably occupied about 1 mm from the filter tip on the secondary side with respect to suction power of a sensor sized as described in the following Example of the present invention. The secondary side portion of the filter 6 was preferably compressed to such a degree that the secondary side portion becomes about ¼ to ⅓ of the primary side portion.

Although it is difficult to express the suction power of the sensor by a numeric value, favorable measurement result (flow rate) was obtained when the spacer 7 is 100 µm in thickness and the filter was compressed to a thickness of 370 µm. The flow rate was low where the filter thickness was 310 µm or less.

Thus, with the sample solution supply pathway 12' formed smaller than the primary side portion of the filter 6 in unit area in cross section, plasma from which hemocytes are removed by the filter 6 is sucked rapidly into the sample solution supply pathway 12' due to capillarity.

In general, the reaction layer is easy to dissolve in one portion and hard to dissolve in other portion. The easy-to-dissolve portion lies along the edge of the sample solution supply part 12', i.e., along the wall surface of the slit 12 of the spacer 7. The hard-to-dissolve portion is a center portion of the reaction layer in the liquid flow direction. Since the sample solution having passed the filter 6 flows along the slit 12 by priority, the sample solution may fill the air aperture in some cases before the center portion of the reaction layer dissolves completely. With the secondary side portion of the filter 6 shaped such that a center thereof is projected inside of the sample solution supply pathway 12' as compared with the right and left, the sample solution flows along the center portion of the sample solution supply pathway 12' by priority. Thereby, the plasma can rapidly be flown into the sensor without leaving bubbles in the center portion of the sample solution supply pathway 12'.

In measurement, a fingertip stung to bleed is placed on the sample solution supply part 30 to supply blood to the filter 6. The blood permeates into the filter 6 from the end face and the top face on the primary side. At this time, with the existence of the third pressing part c serving as a partition, the blood does not travel on the surface of the filter 6 by priority to flow directly into the sample solution supply pathway 12'. Further, since the third and first pressing parts c and a do not agree in position as viewed in a projection on a plane identical to the insulating base plate 1, the expansion of the filter 6 is not inhibited and the possibility of destroying the hemocytes is eliminated.

The electrode system is preferably made of noble metal electrodes. If printed electrodes formed by screen printing are used, accuracy in determining the electrode area becomes poor because the preferable width of the sample solution supply pathway 12' is 1.5 mm or less. On the other hand, the noble metal electrodes allow trimming with laser of 0.1 mm width, which is highly accurate in determining the electrode area.

Hereinafter, an example of the present invention is described, but the invention is not limited thereto.

EXAMPLE

A cholesterol sensor configured as shown in FIGS. 1, 2 and 4 was fabricated in the following manner. An electron mediator was contained in a reaction layer 29 and cholesterol oxidase, cholesterol esterase and a surfactant were contained in a reaction layer 30.

First, 5 µl of 0.5 wt % CMC aqueous solution was dropped onto the electrode system of the insulating base plate 1 and dried in a warm-air dryer at 50° C. for 10 minutes to form a hydrophilic polymer layer 28.

Then, 4 µl of potassium ferricyanide aqueous solution (corresponding to 70 mM of potassium ferricyanide) was dropped onto the hydrophilic polymer layer 28 and dried in the warm-air drier at 50° C. for 10 minutes to form a reaction layer 29 containing potassium ferricyanide. Further, to a solution dissolved therein cholesterol oxidase derived from Nocardia (EC1.1.3.6: ChOD) and cholesterol esterase derived from Pseudomonas (EC.3.1.1.13: ChE), polyoxyethylene (10) octyl phenyl ether (Triton X-100) was added as a surfactant.

The resulting mixture solution was dropped in an amount of 0.4 µl onto a portion of the cover 13 exposed to the sample supply solution pathway 12', preliminarily frozen with liquid nitrogen at −196° C., and then dried using a freeze dryer for 2 hours to form a reaction layer 30 containing 450 U/ml of cholesterol oxidase, 1125 U/ml of cholesterol esterase and 2 wt % of a surfactant.

Glass fiber filter paper of about 300 to 400 µm thick was stamped into the form of an isosceles triangle having a bottom of 3 mm and a height of 5 mm and a tip thereof on the secondary side was rounded to obtain a filter 6. The filter 6 of an almost isosceles triangle shape was disposed between the insulating base plate 1 and the joint base plate A.

Thereafter, the member obtained by disposing the filter 6 between the insulating base plate 1 and the joint base plate A was bonded to the joint base plate B obtained by integrating the spacer 18 and the cover 22, thereby forming a cholesterol sensor configured as shown in FIGS. 1, 2 and 4.

In this sensor, 10 µl of whole blood sample solutions varied in concentration were added to the sample solution supply part 30. Three minutes later, a pulse voltage of +0.2V with reference to the counter electrode was applied to the measuring electrode, i.e., in the anode direction, and then 5 seconds later, a current value between the measuring electrode and the counter electrode was measured. The results are shown in FIG. 5, which is a graph illustrating a relationship between the cholesterol concentration in the whole blood and the current value.

As apparent from FIG. 5, the sensor of the present invention gives favorable linearity between the cholesterol concentration and the current value.

INDUSTRIAL APPLICABILITY

According to the present invention, there is provided an improved biosensor in which plasma stops at an air aperture regardless of the viscosity of the plasma in a sample solution and the plasma volume in whole blood. Thus, the present invention provides a cholesterol sensor of high accuracy and excellent response aimed at measurement of the whole blood.

The invention claimed is:

1. A biosensor comprising an insulating base plate, an electrode system including a measuring electrode and a counter electrode provided on said base plate, a cover for covering said insulating base plate, at least one reaction layer containing oxidoreductase and/or an electron mediator, a sample solution supply pathway which is formed by said insulating base plate and said cover and includes said electrode system and said reaction layer, a first air aperture provided in said cover in said sample solution supply pathway, a sample solution supply part, and a filter provided between said sample solution supply pathway and said sample solution supply part to filter hemocytes, said biosensor being capable of sucking plasma with hemocytes therein filtered with said filter into said sample solution supply pathway due to capillarity, characterized in that a second air aperture is provided in said insulating base plate in said sample solution supply pathway.

2. The biosensor in accordance with claim 1, characterized in that said first air aperture and said second air aperture are communicated.

3. The biosensor of claim 2, wherein said second air aperture is provided at a position contacting said measuring electrode.

* * * * *

UNITED STATES PATENT AND TRADEMARK OFFICE
CERTIFICATE OF CORRECTION

PATENT NO.         : 7,056,425 B2
APPLICATION NO. : 10/469522
DATED                 : June 6, 2006
INVENTOR(S)       : Miwa Hasegawa et al.

It is certified that error appears in the above-identified patent and that said Letters Patent is hereby corrected as shown below:

On the Title page of the Letters Patent;

Under section (75) Inventors, change:

"Tomohiro Yamamoto, Hirakata (JP)" to -- Tomohiro Yamamoto, Osaka (JP) --,

"Shin Ikeda, Katano (JP)" to -- Shin Ikeda, Osaka (JP) --,

"Toshihiko Yoshioka, Hirakata (JP)" to -- Toshihiko Yoshioka, Osaka (JP) --

Add – (30) Foreign Application Priority Data, Nov. 14, 2001......JP 2001-349069 --

Signed and Sealed this

Fifteenth Day of May, 2007

JON W. DUDAS
*Director of the United States Patent and Trademark Office*